(12) United States Patent
Monetti et al.

(10) Patent No.: US 10,857,589 B2
(45) Date of Patent: Dec. 8, 2020

(54) THREE-DIMENSIONAL COMPLEX COIL

(71) Applicant: MicroVention, Inc., Aliso Viejo, CA (US)

(72) Inventors: Richard Monetti, San Clemente, CA (US); George Martinez, Brea, CA (US); Matthew J. Fitz, Vista, CA (US); Damian Jonathan Perez, Laguna Hills, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 0 days.

(21) Appl. No.: 16/105,634

(22) Filed: Aug. 20, 2018

(65) Prior Publication Data

US 2018/0354020 A1    Dec. 13, 2018

Related U.S. Application Data

(63) Continuation of application No. 15/360,140, filed on Nov. 23, 2016, now Pat. No. 10,081,048, which is a
(Continued)

(51) Int. Cl.
*A61B 17/00* (2006.01)
*A61B 17/12* (2006.01)
*B21F 45/00* (2006.01)

(52) U.S. Cl.
CPC ........ *B21F 45/008* (2013.01); *A61B 17/1214* (2013.01); *A61B 17/1215* (2013.01);
(Continued)

(58) Field of Classification Search
CPC ...... B21F 45/008; B21F 45/00; B21F 35/003; B21F 3/10; A61B 17/1214;
(Continued)

(56) References Cited

U.S. PATENT DOCUMENTS 1,594,292 A    7/1926  Zierick
1,645,941 A   10/1927  Williams
(Continued)

FOREIGN PATENT DOCUMENTS

JP      H0466235 A     3/1992
JP      2005-152856 A  6/2005
(Continued)

OTHER PUBLICATIONS

United States Patent and Trademark Office, Notice of Allowance dated Aug. 24, 2016 in U.S. Appl. No. 13/278,008, 8 pages.
(Continued)

*Primary Examiner* — Ryan J. Walters
*Assistant Examiner* — Lawrence Averick
(74) *Attorney, Agent, or Firm* — Inskeep IP Group, Inc.

(57) ABSTRACT

A complex coil and a fixture for forming same configured such that loops are formed having various configurations relative to each other. The configurations provide improved thrombus formation and reduced rotation or tumbling once implanted. The complex coil is formed of a material that may deformed for purposes of placing the complex coil into a catheter and returns to a complex shape that includes said loops once deployed.

18 Claims, 10 Drawing Sheets

Related U.S. Application Data continuation of application No. 13/278,008, filed on Oct. 20, 2011, now Pat. No. 9,533,344, which is a continuation of application No. 11/560,251, filed on Nov. 15, 2006, now Pat. No. 8,066,036.

(60) Provisional application No. 60/822,656, filed on Aug. 17, 2006, provisional application No. 60/738,087, filed on Nov. 17, 2005.

(52) U.S. Cl.
CPC .... *A61B 17/1219* (2013.01); *A61B 17/12022* (2013.01); *A61B 17/12145* (2013.01); *A61B 17/12154* (2013.01); *B21F 45/00* (2013.01); *A61B 2017/00526* (2013.01); *A61B 2017/00867* (2013.01)

(58) Field of Classification Search
CPC ........ A61B 17/12022; A61B 17/12145; A61B 17/1215; A61B 17/12154; A61B 17/1219; A61B 2017/00526; A61B 2017/00867
USPC ......... 29/888–890.09, 890.11–899.1, 2.1–25, 29/76.1–91.8, 284, 401.1–559, 592, 29/700–728, 765–824, 605, 606, 165, 29/180, 182; 606/200; 72/137
See application file for complete search history.

(56) References Cited

U.S. PATENT DOCUMENTS

| | | | |
|---|---|---|---|
| 1,653,951 A | 12/1927 | Featherstone | |
| 2,296,356 A | 9/1942 | Lindenblad | |
| 2,825,169 A | 3/1958 | Ciroli | |
| 3,154,457 A | 10/1964 | Ranoha | |
| 3,482,126 A | 12/1969 | Bradley | |
| 4,957,501 A | 9/1990 | Lahille et al. | |
| 4,994,069 A | 2/1991 | Ritchart et al. | |
| 5,108,407 A | 4/1992 | Geremia et al. | |
| 5,350,398 A | 9/1994 | Pavcnik et al. | |
| 5,382,259 A | 1/1995 | Phelps et al. | |
| 5,522,822 A | 6/1996 | Phelps et al. | |
| 5,536,274 A | 7/1996 | Neuss | |
| 5,549,624 A | 8/1996 | Mirigian et al. | |
| 5,639,277 A | 6/1997 | Mariant et al. | |
| 5,645,558 A | 7/1997 | Horton | |
| 5,676,697 A | 10/1997 | McDonald | |
| 5,766,219 A | 6/1998 | Horton | |
| 5,909,130 A | 6/1999 | Martin et al. | |
| 5,911,731 A | 6/1999 | Pham et al. | |
| 5,935,148 A | 8/1999 | Villar et al. | |
| 5,957,948 A | 9/1999 | Mariant | |
| 6,004,448 A | 12/1999 | Ken et al. | |
| 6,010,498 A | 1/2000 | Guglielmi | |
| 6,090,125 A | 7/2000 | Horton | |
| 6,171,326 B1 | 1/2001 | Ferrera et al. | |
| 6,193,728 B1 | 2/2001 | Ken et al. | |
| 6,231,586 B1 | 5/2001 | Mariant | |
| 6,280,457 B1 | 8/2001 | Wallace et al. | |
| 6,322,576 B1* | 11/2001 | Wallace ........... | A61B 17/12022 606/191 |
| 6,478,773 B1 | 11/2002 | Gandhi et al. | |
| 6,585,756 B1 | 7/2003 | Strecker | |
| 6,589,265 B1 | 7/2003 | Palmer et al. | |
| 6,605,101 B1 | 8/2003 | Schaefer et al. | |
| 6,635,068 B1 | 10/2003 | Dubrul et al. | |
| 6,635,069 B1* | 10/2003 | Teoh ................ | A61B 17/12022 606/191 |
| 6,638,291 B1 | 10/2003 | Ferrera et al. | |
| 6,860,893 B2 | 3/2005 | Wallace et al. | |
| 6,929,654 B2* | 8/2005 | Teoh ................ | A61B 17/12022 606/200 |
| 6,990,729 B2 | 1/2006 | Pleskach et al. | |
| 7,107,666 B2 | 9/2006 | Hiatt et al. | |
| 7,608,086 B2 | 10/2009 | Tanaka et al. | |
| 2002/0019647 A1* | 2/2002 | Wallace ........... | A61B 17/12022 606/200 |
| 2002/0107534 A1 | 8/2002 | Schaefer et al. | |
| 2002/0128671 A1 | 9/2002 | Wallace et al. | |
| 2003/0005569 A1 | 1/2003 | Hiatt et al. | |
| 2003/0224183 A1* | 12/2003 | Warburton-Pitt ....... | B29C 43/18 428/447 |
| 2005/0192618 A1 | 9/2005 | Porter | |
| 2005/0192621 A1 | 9/2005 | Wallace et al. | |

FOREIGN PATENT DOCUMENTS

| | | |
|---|---|---|
| WO | WO1990/06563 A2 | 9/1990 |
| WO | WO1994/009705 A1 | 5/1994 |
| WO | WO2000/074577 A1 | 12/2000 |

OTHER PUBLICATIONS

United States Patent and Trademark Office, Final Office Action dated Jun. 3, 2016 in U.S. Appl. No. 13/278,008, 6 pages.
United States Patent and Trademark Office, Final Office Action dated Jun. 8, 2015 in U.S. Appl. No. 13/278,008, 10 pages.
United States Patent and Trademark Office, Office Action dated Jul. 26, 2013 in U.S. Appl. No. 13/278,008, 25 pages.
United States Patent and Trademark Office, Office Action dated Nov. 26, 2014 in U.S. Appl. No. 13/278,008, 11 pages.
United States Patent and Trademark Office, Notice of Allowance dated Jul. 26, 2011 in U.S. Appl. No. 11/560,251, 8 pages.
United States Patent and Trademark Office, Office Action dated Dec. 8, 2010 in U.S. Appl. No. 11/560,251, 12 pages.
United States Patent and Trademark Office, Final Office Action dated Aug. 6, 2010 in U.S. Appl. No. 11/560,251, 10 pages.
United States Patent and Trademark Office, Office Action dated Apr. 5, 2010 in U.S. Appl. No. 11/560,251, 10 pages.

\* cited by examiner

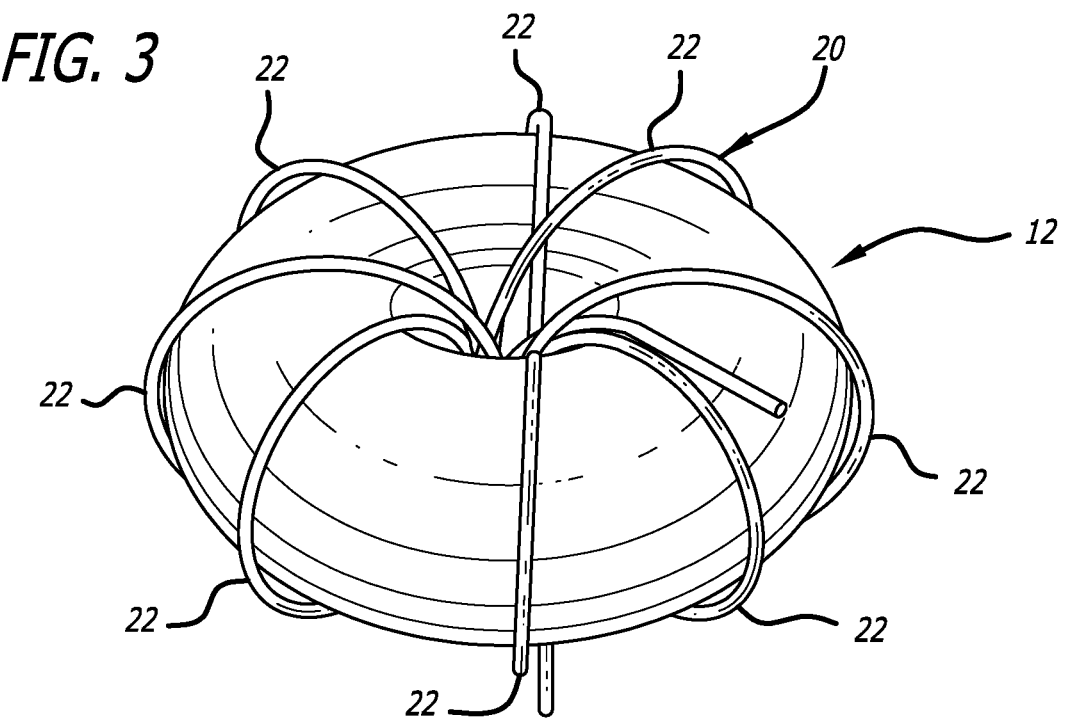
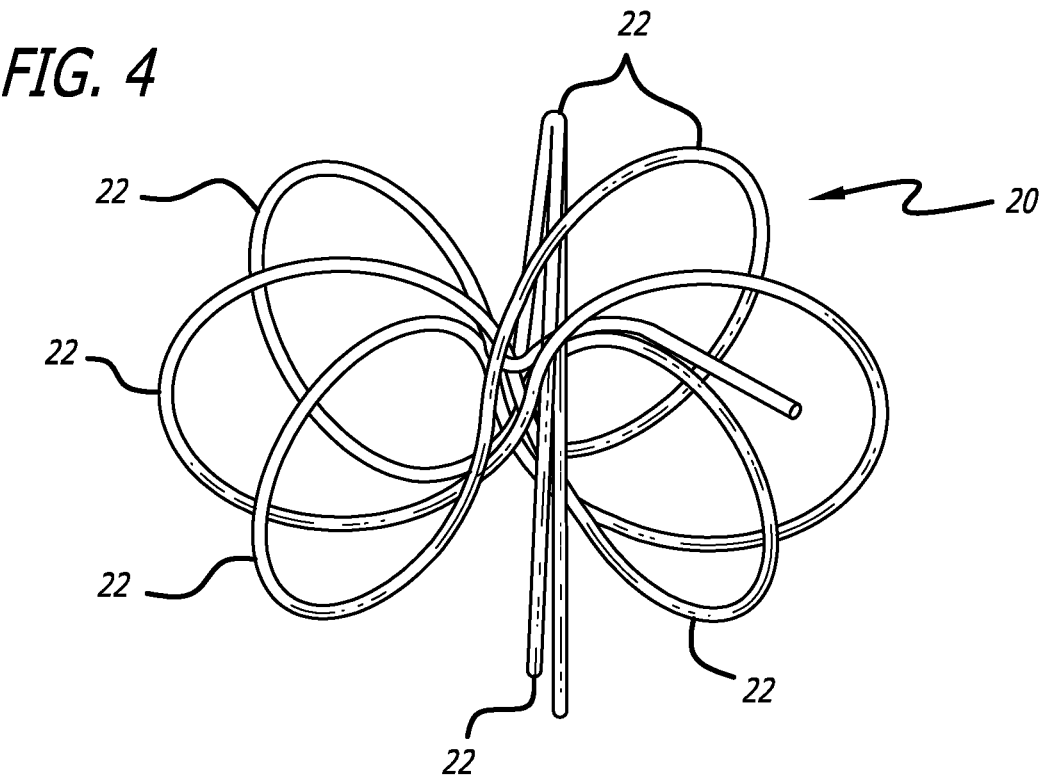

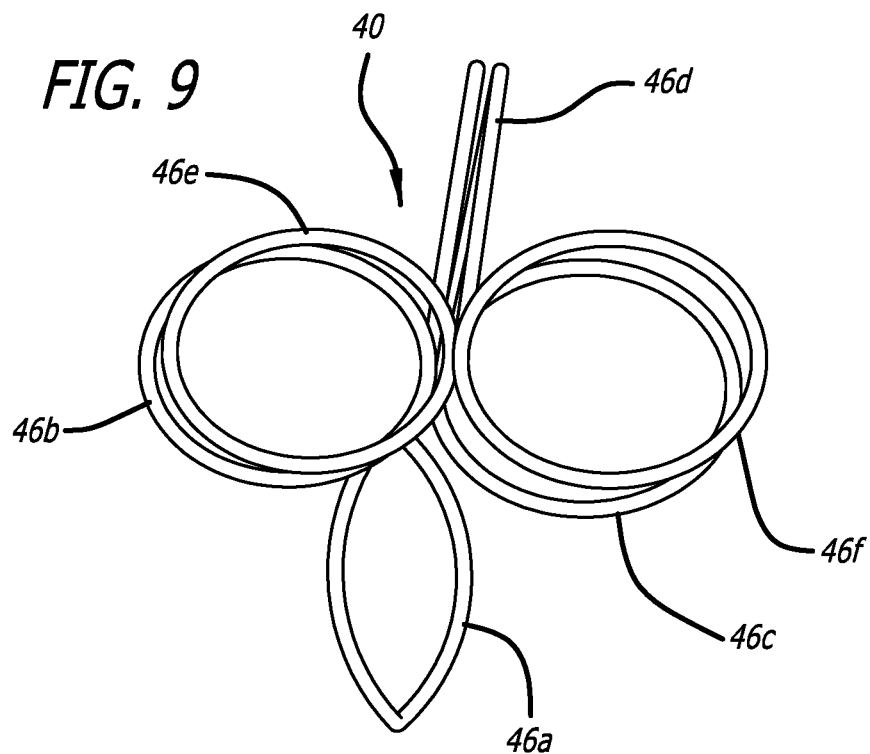
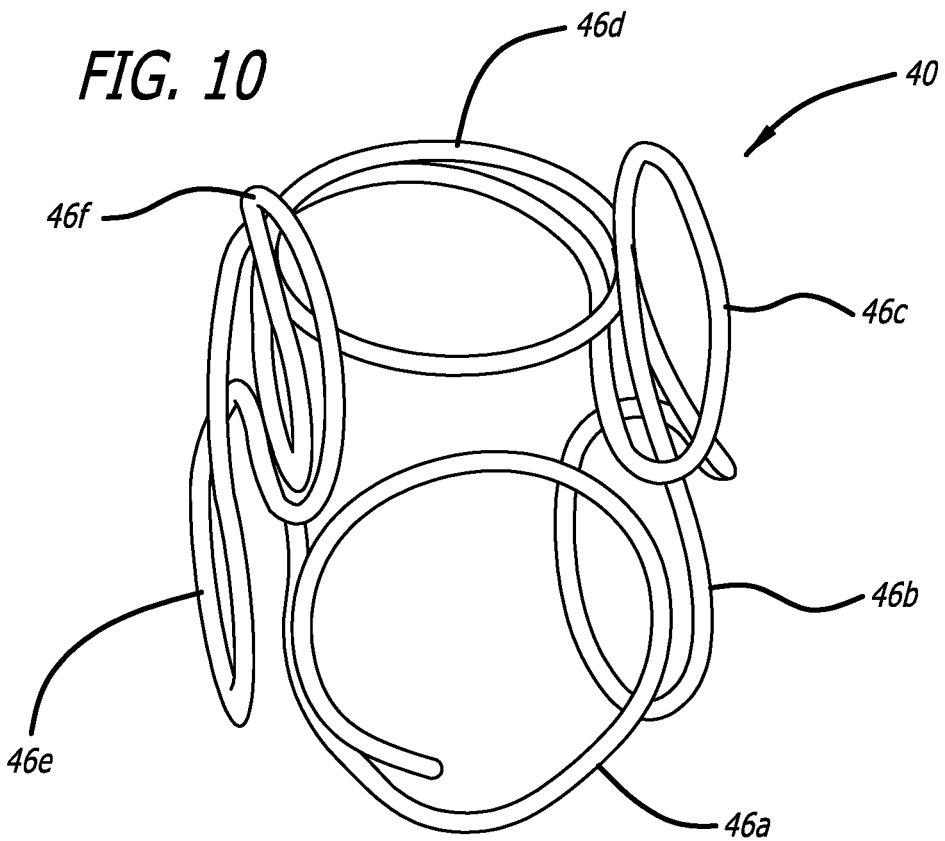

THREE-DIMENSIONAL COMPLEX COIL

CROSS-REFERENCE TO RELATED DOCUMENTS

This application is a continuation of U.S. patent application Ser. No. 15/360,140 filed Nov. 23, 2016 entitled Three-Dimensional Complex Coil, which is a continuation of U.S. patent application Ser. No. 13/278,008 filed Oct. 20, 2011 entitled Three-Dimensional Complex Coil (now U.S. Pat. No. 9,533,344 issued Jan. 3, 2017), which is a continuation of U.S. patent application Ser. No. 11/560,251 filed Nov. 15, 2006 entitled Three-Dimensional Complex Coil (now U.S. Pat. No. 8,066,036 issued Nov. 29, 2011), which claims priority from U.S. Provisional Patent Application Ser. No. 60/738,087, filed Nov. 17, 2005 entitled Three Dimensional Complex Coil and U.S. Provisional Patent Application Ser. No. 60/822,656, filed Aug. 17, 2006 entitled Three Dimensional Complex Coil, all of which are hereby incorporated by reference in their entireties.

BACKGROUND OF THE INVENTION

The prior art contemplates a number of methods and devices for treating a body aneurysm using three-dimensional (3-D) shaped coils, sometimes referred to as "complex" coils. For example, Horton U.S. Pat. No. 5,766,219, the contents of which are incorporated by reference, shows a hollow structure. Phelps U.S. Pat. No. 5,382,259 and Ritchart U.S. Pat. No. 4,994,069, the contents of which are incorporated by reference, show other 3-D coil designs. Teoh U.S. Pat. No. 6,635,069, the contents of which are incorporated by reference, teaches a series of non-overlapping loops. Wallace U.S. Pat. No. 6,860,893, the contents of which are incorporated by reference, shows complex coils. Ferrera U.S. Pat. No. 6,638,291, the contents of which are incorporated by reference, shows a device similar to Teoh's and Wallace's except that a J-shaped proximal segment extends away from the complex portion of the device.

The following patents provide further background and are also incorporated herein by reference: Guglielmi U.S. Pat. No. 6,010,498; Gandhi U.S. Pat. No. 6,478,773; Schaefer 2002/0107534; Mariant U.S. Pat. No. 5,957,948; Pham U.S. Pat. No. 5,911,731; Lahille U.S. Pat. No. 4,957,501; Porter 2005/0192618; Wallace 2005/0192621.

There is, however an ongoing need to provide more advanced and improved complex coils so as to provide better treatment of an aneurysm.

OBJECTS AND SUMMARY OF THE INVENTION

It is therefore an object of the invention to provide improved devices and methods for treating an aneurysm over the prior art.

This object and other objects not specifically enumerated here are addressed by the invention, at least one embodiment of which includes a toroid-shaped device wound around a fixture such that portions of the device's length meet or overlap in the center of the toroid. This allows the outer portion of the device to form a scaffold while the interior portion of the device provides occlusion to prevent the influx of blood and promote thrombus formation.

One embodiment includes a strand of material that self-forms into a toroid-shaped series of loops and is designed to provide a stable structure within the body cavity, allowing for occlusion of the cavity and serving as a framework to hold additional treatment devices.

Another embodiment of the present invention provides a strand of material that self-forms into a cruciform series of loops and is designed to provide a stable structure within the body cavity, allowing for occlusion of the cavity and serving as a framework to hold additional treatment devices.

In another aspect, the invention includes tools and methods of manufacture to make the aforementioned embodiments of the invention.

In yet another aspect of the present invention, an embodiment includes a cruciform device wound around a fixture comprising at least two parallel pins disposed at an angle to at least one additional pin. This construction allows the outer portion of the device to form a scaffold while the interior portion of the device provides occlusion to prevent the influx of blood and promote thrombus formation. This embodiment also advantageously resists rotating or tumbling during deployment.

BRIEF DESCRIPTION OF THE DRAWINGS

FIG. 3 is a perspective view of an embodiment of a fixture and a complex coil of the present invention;

FIG. 4 is a perspective view of a complex coil of the present invention;

FIGS. 9-10 are photographs of complex coils formed according to one of the methods of the present invention;

DETAILED DESCRIPTION OF THE INVENTION

Toroid Three-Dimensional Coil

Referring now to the figures and first to FIGS. 1-6, a coil or complex coil 10 is described that is shaped using a toroid-shaped fixture 12. The coil 10 has been wrapped around the fixture 12 four times in FIG. 1 such that four loops 14 are formed, each loop being positioned approximately 90 degrees from the adjacent loops. Wrapping the coil 10 around the fixture 12 causes the coil 10 to form into a complex shape when deployed into a body cavity such as a blood vessel or aneurysm. The device may be made from a length of wire that has been helically wound to form an elongate coil wire. Alternatively, the wire may be braided or knitted by methods known in the art to form a secondary shape. The wire is preferably a memory metal, such as Nitinol, but may be platinum, tantalum, tungsten, stainless steel, or other biocompatible material. Other materials, such as Dacron or Nylon fibers, biodegradable polymers such as polylactic or polyglycolic acid, and expansible or non-expansible hydrogel materials may be placed inside or outside the coil or braid structure to enhance the performance of the device.

Figure 1:
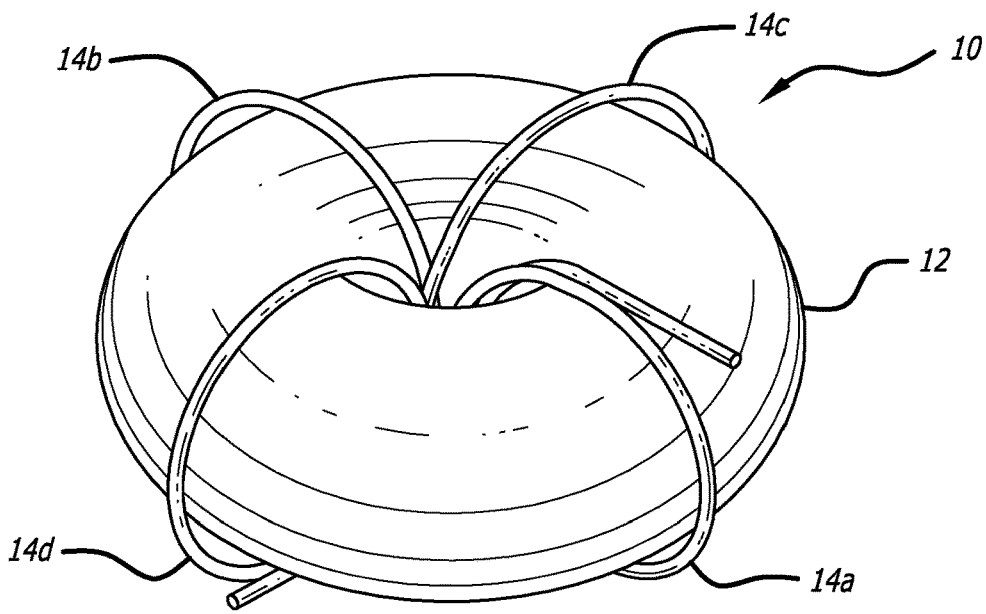
FIG. 1 is a perspective view of an embodiment of a fixture and a complex coil of the present invention.
Figure 2:
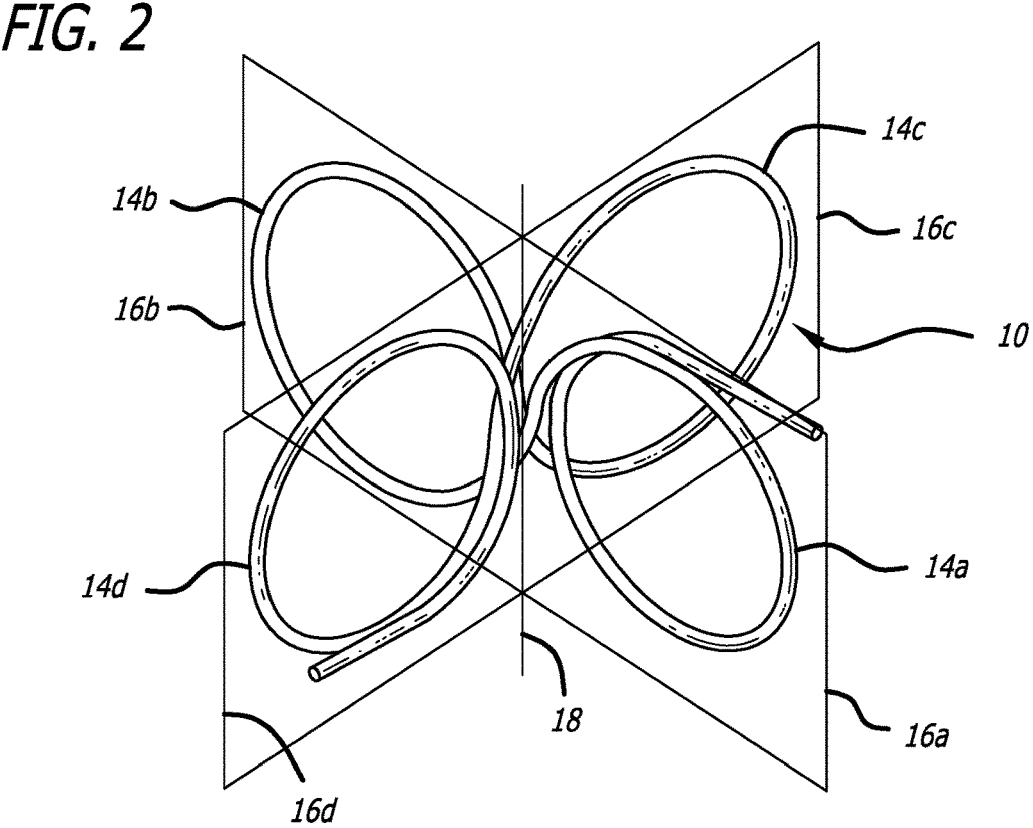
FIG. 2 is a perspective view of an embodiment of a complex coil of the present invention.

For purposes of description only, an observation may be made regarding the shape of the complex coil 10 that results from wrapping the coiled wire around the toroid-shaped fixture 12. As illustrated in FIG. 2, each of the loops 14*a-d* is roughly contained within respective planes 16*a-d*. The planes intersect with each other at approximately a common intersection axis 18 near the center of the complex coil 10. As one skilled in the art will realize, any loops formed around the toroid fixture 12 will only approximately be contained within such planes and the degree to which they are contained within these planes is only a function of how they are wound around the toroid and has little or no effect on their performance.

As shown in FIGS. 3 and 4, any number of loops may be used in forming a complex coil of the present invention. In FIG. 3, a complex coil 20 is formed by wrapping eight loops 22 around the toroid-shaped fixture 12. The loops 22 are relatively evenly spaced around the toroid 12 but may be spaced in any number of configurations. The result is the eight-looped complex coil 20 shown in FIG. 4.

Figure 5:
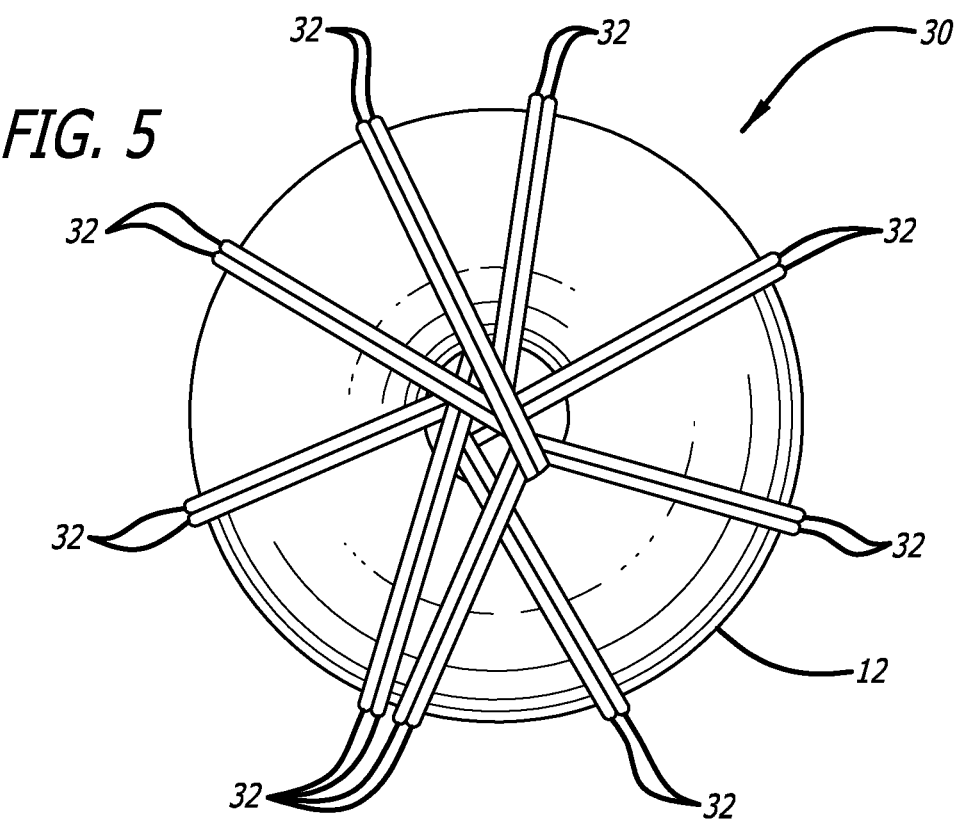
FIGS. 5-8 are photographs of a complex coils around various fixtures of the present invention.
Figure 6:
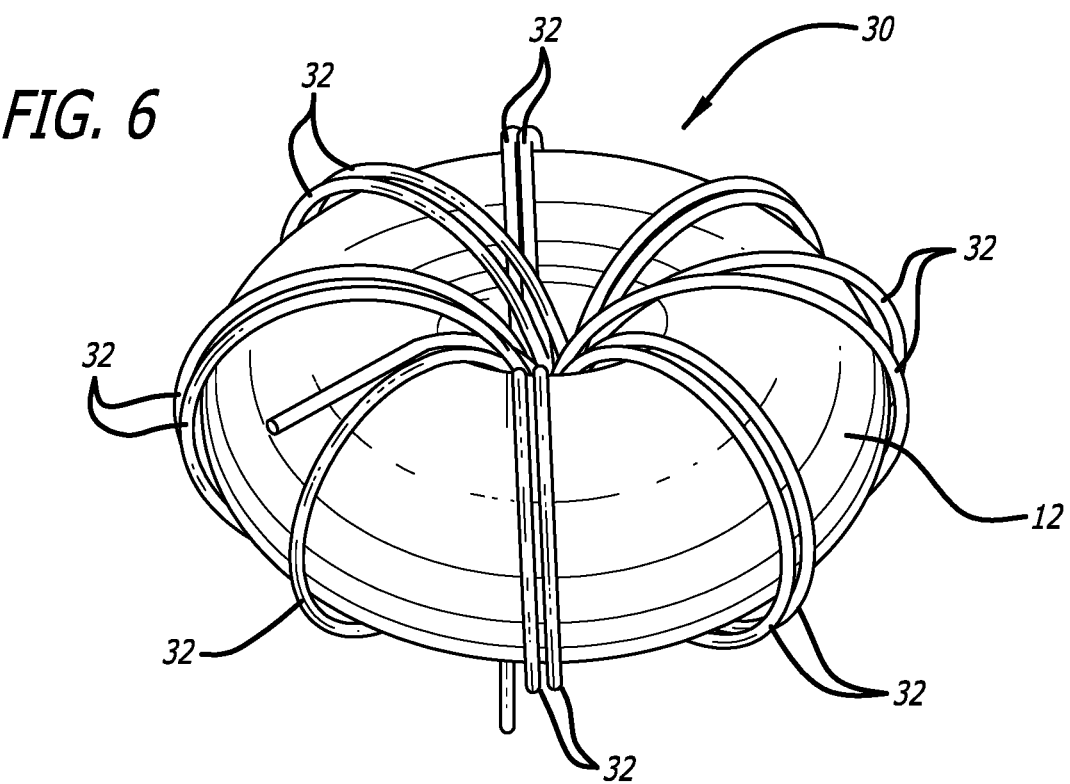

FIGS. 5 and 6 show complex coils 30 being formed around a toroid fixture 12 using 16 loops 32. The loops 32 are grouped in sets of two such that only eight distinct loops appear.

One example used to treat conditions, such as cerebral aneurysms, includes a platinum/tungsten alloy complex coil (92% Pt, 8% W available from Sigmund Cohn Mount Vernon, N.Y.) with a diameter in the range of about 0.125 mm to about 0.625 mm and a length of about 5 mm to about 1000 mm. The complex coil is formed around a ceramic or metallic toroid-shaped fixture similar to the fixtures 12 shown in FIGS. 1, 3, 5, and 6. The winding pattern shown in FIGS. 1-6 forms a first loop 14*a* around the toroid 12, then a second loop 14*b* approximately 180° around the toroid from the first loop. In this example, a FIG. 8 pattern is used to wind the first and second loops. A third loop 14*c* is then formed at an angle around the center of the toroid, typically 5° to 175°, to the second loop. A fourth loop 14*d* is formed using a FIG. 8 pattern from the third loop 14*c*. More loops 14 may be added depending on the desired device size.

Those skilled in the art will appreciate that one advantage to the toroid complex coil configuration is that it may be scaled to the size of the treatment site by changing the number of loops. For example, very small (0.5-3 mm) lesions may be treated with 2 to 4 loop configurations, medium sized (4-10 mm) with 4-12 loop configurations, large (over 10 mm) with 8-36 loop configurations, and so on. The loops can form a closed structure such as an "O" shape (e.g. circle, oval, square, ellipse, star, etc.) or can be open such as a "C" or "U" shape. The loops may be of any dimension and are typically scaled to the approximate size of the treatment site. In the previous example, the loops may range from 0.5 mm diameter to 50 mm diameter. In this regard, "diameter" should not be narrowly construed to imply a circular dimension. Rather, "diameter" is used broadly to encompass the approximate size and shape of a loop.

After winding, the fixture and complex coil are heat-set by methods known in the art. For example, a typical annealing step for platinum complex coils is approximately 1100° F. for 5-40 minutes.

Once annealed, the complex coil will approximately retain the wound shape when substantially unconstrained or in its minimum energy state. The complex coil may then be subject to further processing such as forming a tip, adding a coupling mechanism for attachment to a delivery system, placing hydrogel or fibers onto or within the complex coil, placing a stretch resistant member inside or outside the complex coil, etc. The complex coil can then be attached to a delivery system, which is well known in the art, such as those disclosed in U.S. patent application Ser. No. 11/212,830, entitled Thermal Detachment System for Implantable Devices, the entirety of which is incorporated by reference hererin. Other examples of delivery systems are disclosed in Guglielmi U.S. Pat. No. 6,010,498 or Gandhi U.S. Pat. No. 6,478,773. Once attached to the delivery pusher, the complex coil is placed in a substantially linear configuration within a tube for delivery to the treatment site.

In a typical procedure, the linear complex coil is fed through a conduit such as a microcatheter by advancing it through the conduit with the delivery pusher. Upon exiting the microcatheter, the complex coil then self-forms into a structure within the treatment site that approximates its annealed shape.

The fixture 12 used to create the implant is shown as a closed circular toroid. However, other non-circular shapes such as elliptical, square, and star-shaped patterns may be used. In addition, the toroid does not need to be a closed structure. In fact, it may be easier to wind if a gap is left within the structure so that tension can be kept on the complex coil by hanging a weight.

Cruciform Three-Dimensional Coil

Referring now to FIGS. 7-12, the production of complex coils 40 are shown using a fixture 42 that includes a plurality of pins 44 arranged at right angles to each other. Like the embodiments shown in FIGS. 1-6, the embodiments of the complex coils 40 formed using the fixture 42 in FIGS. 7-12 may be made from a length of wire that has been helically wound to form a coiled wire. Alternatively, the wire may be braided or knitted by methods known in the art to form a secondary shape. The wire may be platinum, tantalum, tungsten, stainless steel, Nitinol, or other biocompatible material. Other materials, such as Dacron or Nylon fibers, biodegradable polymers such as polylactic or polyglycolic acid, and expansible or non-expansible hydrogel materials may be placed inside or outside the complex coil or braid structure to enhance the performance of the device. By way of example only, one embodiment might be used to treat such conditions as cerebral aneurysms, employs a platinum/tungsten alloy complex coil 10 (92% PT, 8% W available from Sigmund Cohn Mount Vernon, N.Y.) with a diameter in the range of about 0.125 mm to about 0.625 mm and a length of about 5 mm to about 1000 mm.

Figure 7:
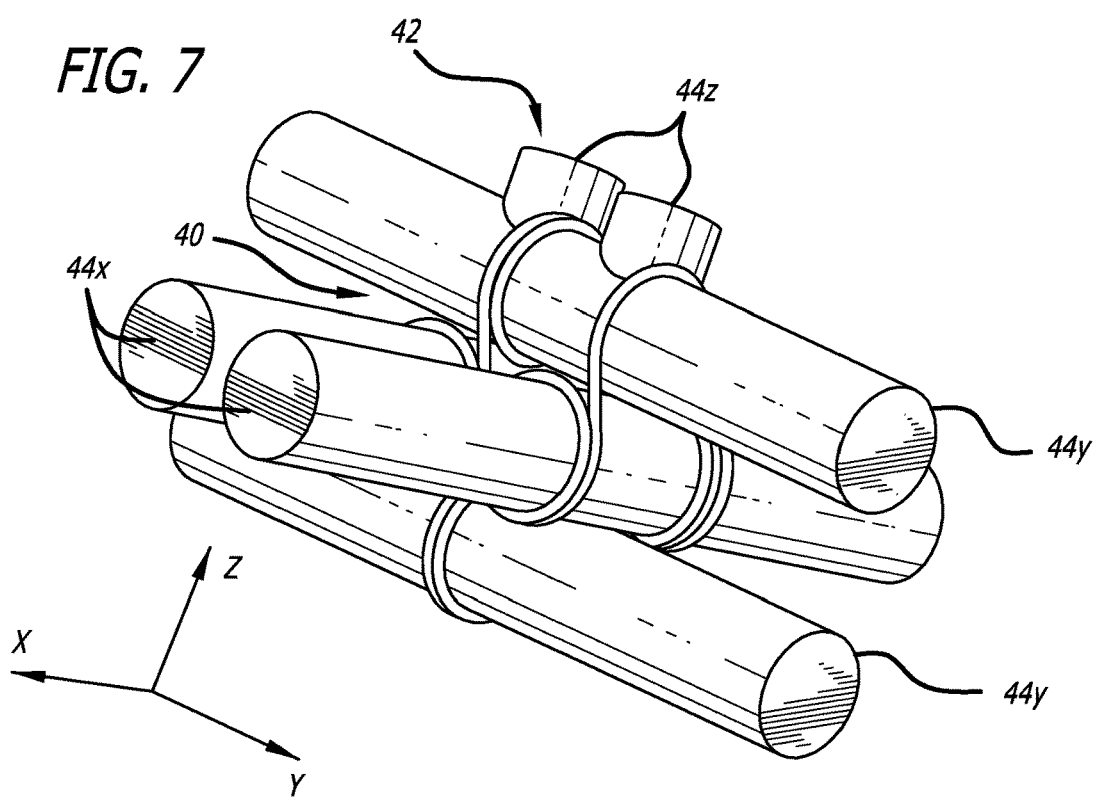
Figure 8:
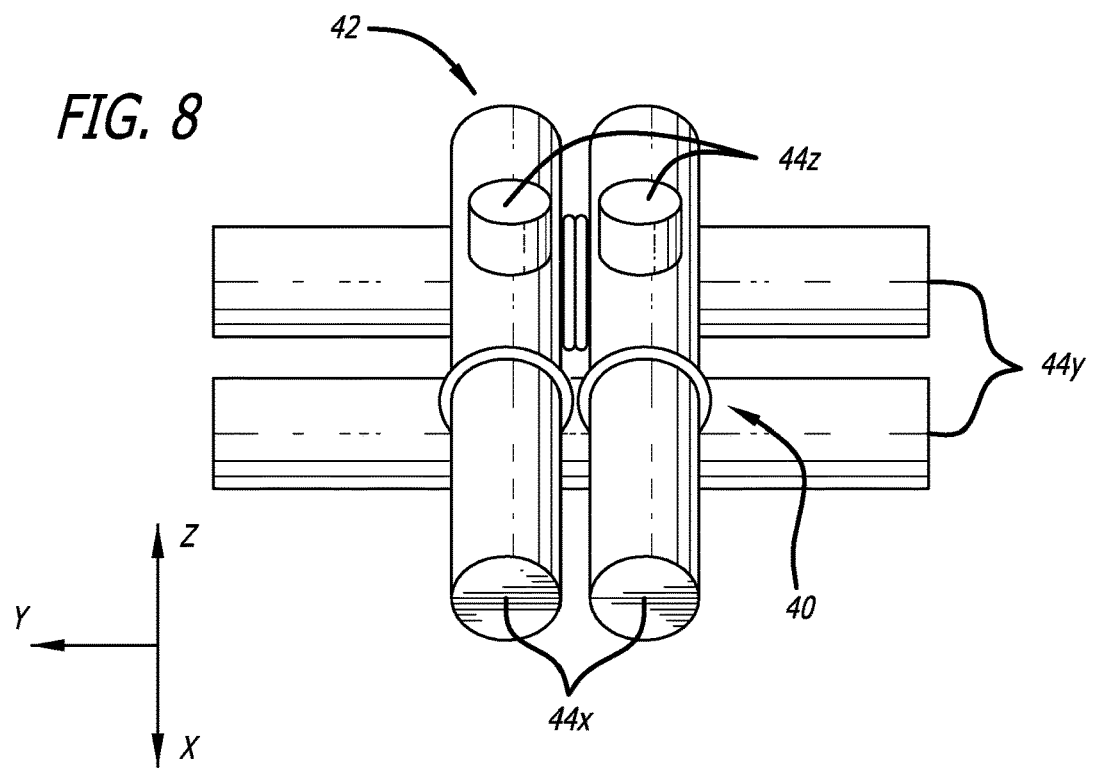
Figure 11:
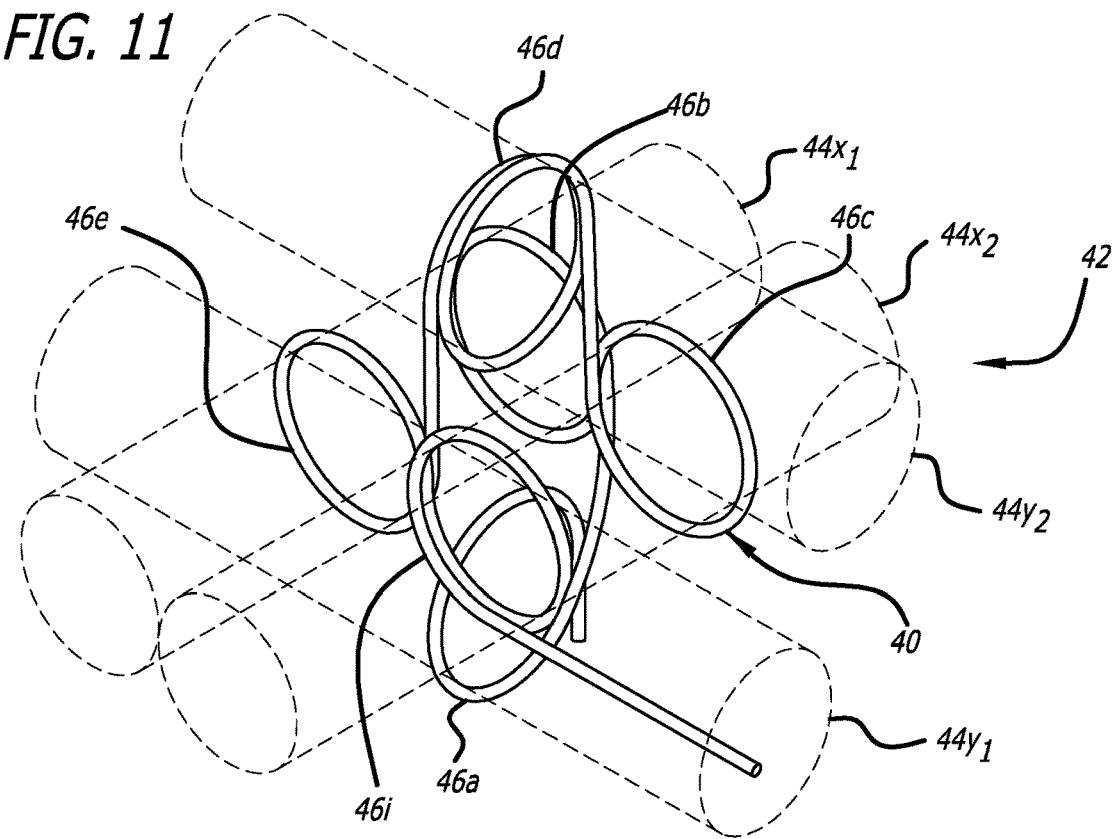
FIG. 11 is a perspective view of an embodiment of a complex coil of the present invention formed around an embodiment of a fixture of the present invention shown in phantom lines.
Figure 12:
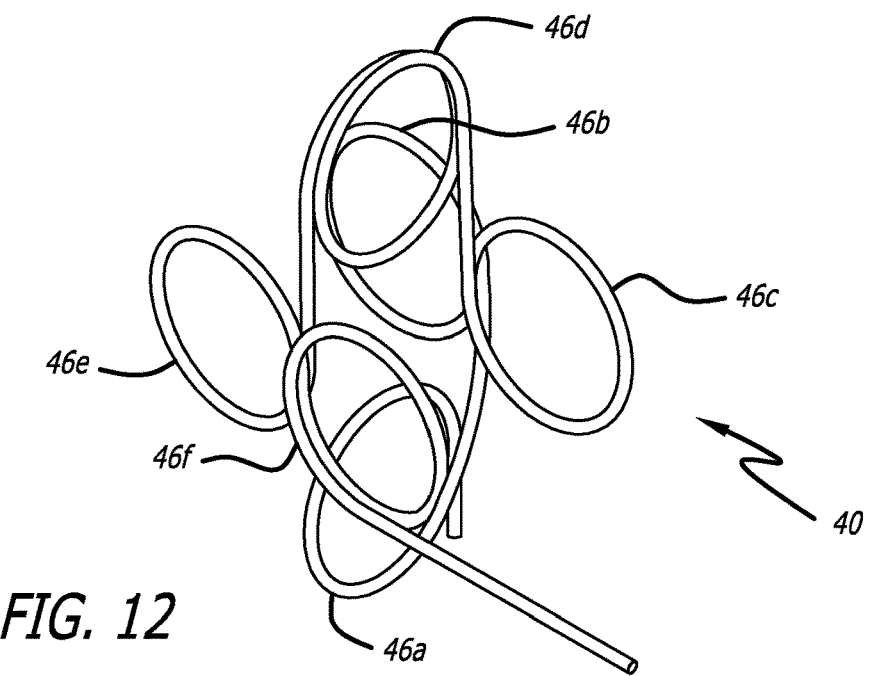
FIG. 12 is a perspective view of an embodiment of a complex coil of the present invention.

The complex coil 40 is formed by wrapping a coiled wire around the fixture 42, as shown in FIGS. 7-8. The fixture 42 is preferably a ceramic or metallic cruciform fixture and includes a plurality of pins 44 arranged at right angles to each other along axes x, y, and z. More specifically, the fixture 42 includes two pins 44*x* that are parallel to the x-axis, two pins 44*y* that are parallel to the y-axis, and two pins 44*z* that are parallel to the z-axis.

An example of a complex coil 40 that can be made using the fixture 42 of FIGS. 7-8 is shown in FIGS. 9-12. The winding pattern in this embodiment, shown most clearly in FIGS. 11-12, forms a first loop 46a around a first pin 44y₁, then a second loop 46b around a second pin 44x₁ that is disposed at an angle to the first pin 44y₁. In this embodiment the angle between the loops 46a and 46b is approximately 45°-135°. A third loop 46c is then formed in approximately the same plane as the second loop 46b. In this example, the third loop 46c is formed around pin 44x₂ in a FIG. 8 pattern with the second loop 46b. A fourth loop 46d is then formed at an angle with the third loop 46c. In this example, the fourth loop 46d is approximately 45°-135° to the third loop and is formed around pin 44y₂ and is also approximately coplanar to the first loop 46a. A fifth loop 46e is then formed at an angle to the fourth loop 46d by wrapping the wire around pin 44x₁ spaced apart from loop 46b, also formed around pin 44x₁. A sixth loop 46f lies in approximately the same plane as the fifth loop 46e in a FIG. 8 pattern with the fifth loop 46e. The sixth loop 46f is formed by wrapping the wire around pin 44x₂ spaced apart from loop 46c, which is also formed around pin 44x₂. In this example, the fifth loop 46e and the sixth loop 46f are approximately concentric with the second loop 46b and the third loop 46c, respectively.

Fewer than six loops may be used to form shorter complex coils, while additional loops may be wound to make a longer device. For example, the pins 44z shown in FIGS. 7-8 extend through the pins 44x and 44y and are thus being used to hold the pins 44x and 44y in place. However, if a longer device is desired, loops could be formed by wrapping wire around the portions of the pins 44z extending from the pins 44y.

Furthermore, those skilled in the art will appreciate that the same final result could be obtained by reversing the just-described winding pattern: i.e. winding a first loop around a first pin, winding a second loop in approximately the same plane as the first loop, winding a third loop at an angle to the second loop, winding a fourth loop at an angle to the third loop, winding a fifth loop in approximately the same plane as the fourth loop, winding a sixth loop at an angle to the fifth loop, and so on.

The loops can form a closed structure such as an "O" shape (e.g. circle, oval, square, ellipse, star, etc.) or can be open such as a "C" or "U" shape. The loops may be of any dimension and are typically scaled to the approximate size of the treatment site. In the previous example, the loops may range from 0.5 mm diameter to 50 mm diameter. In this regard, "diameter" should not be narrowly construed to imply a circular dimension. Rather, diameter is used broadly to encompass the approximate size and shape of a loop.

Figure 13:
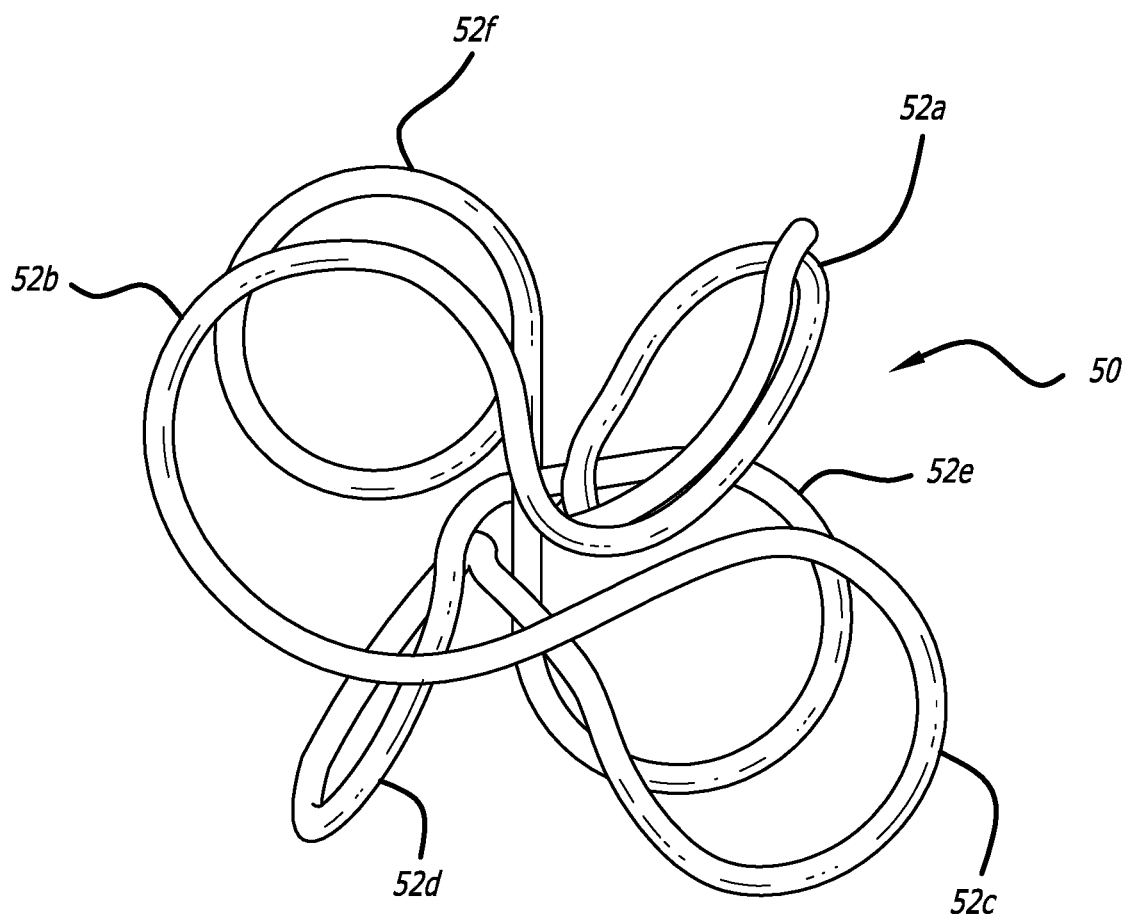
FIG. 13 is a perspective view of an embodiment of a complex coil of the present invention.

For example, the coil 50 shown in FIG. 13 has loops 52 that are open and closed. The open loops are formed by wrapping a wire around a pin but transitioning to an adjacent pin prior to completing an overlapping loop. More specifically, the complex coil 50 of FIG. 13 has six loops 52a-f formed using the fixture 42 of FIGS. 7 and 8. Loop 52a is a complete loop formed around one of the pins 44y. The wire is then wrapped in a FIG. 8 pattern around two adjacent pins 44x to form open loops 52b and 52c. The wire is next wrapped completely around the other y pin, 44y to form complete loop 52d. Next, the wire is wrapped in a FIG. 8 pattern around the two pins 44y on the opposite side of pins 44x to form loops 52e and 52f. The loop 52e is open but the loop 52f is closed, being the last loop.

Figure 14:
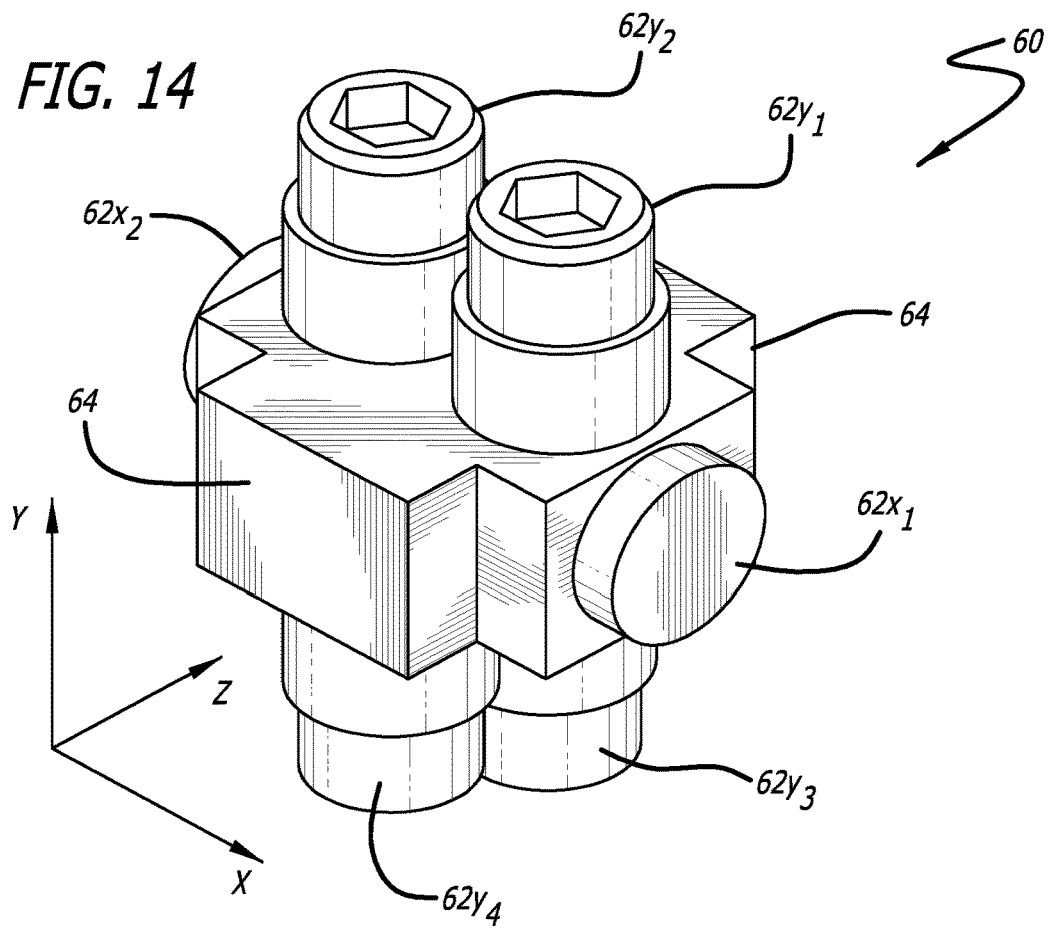
FIG. 14 is a perspective view of an embodiment of a fixture of the present invention.
Figure 15:
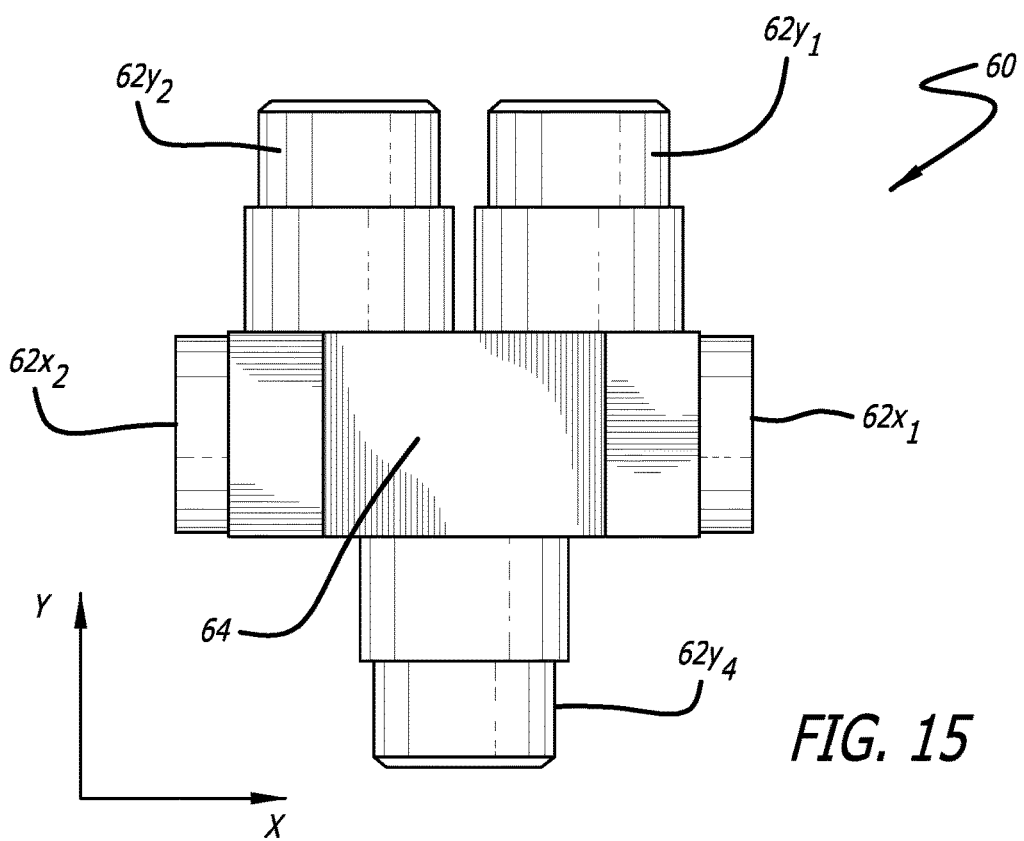
FIG. 15 is a front elevation of the fixture shown in FIG. 14.
Figure 16:
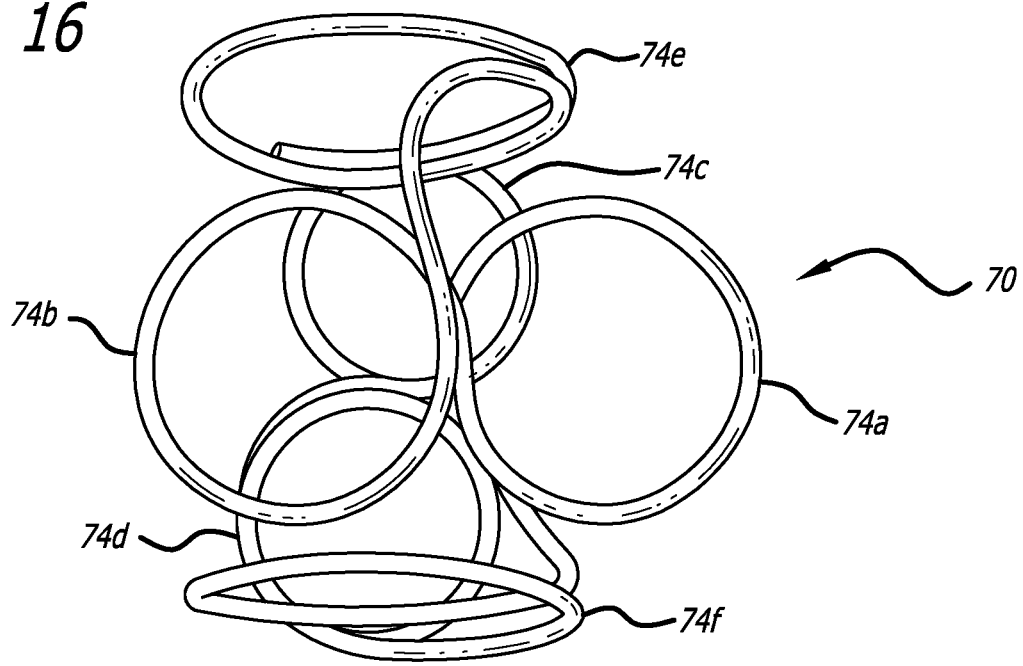
FIGS. 16-19 are photographs of several complex coils formed using methods and fixtures according to the present invention.
Figure 17:
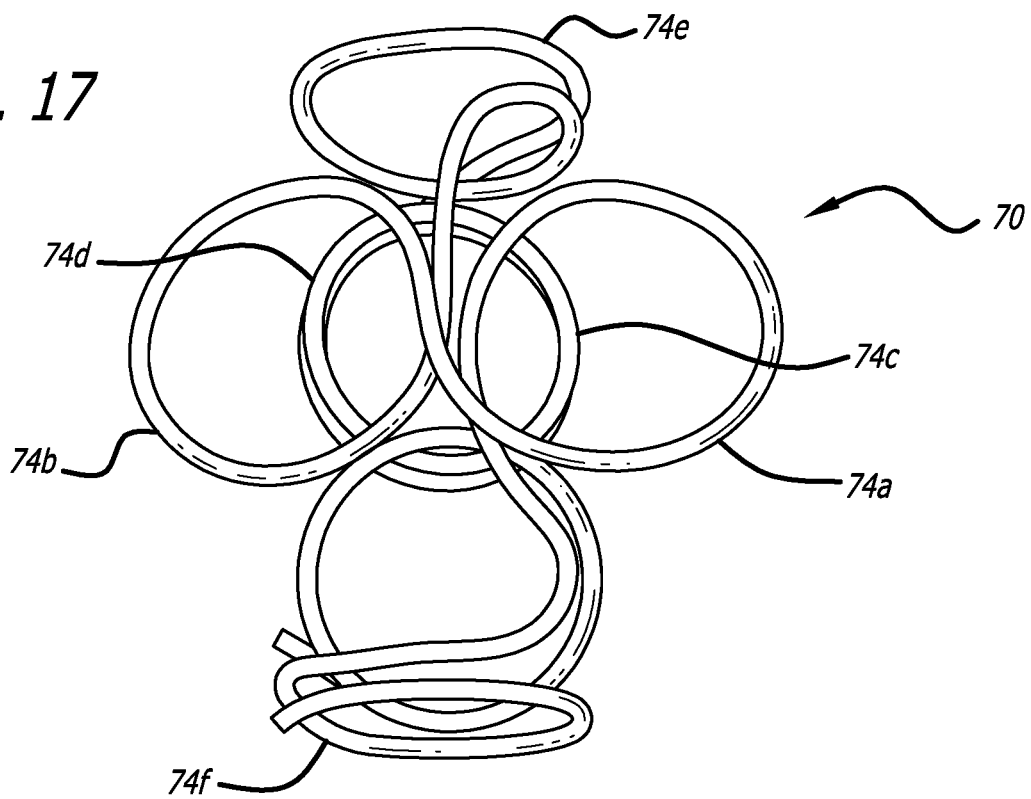
Figure 18:
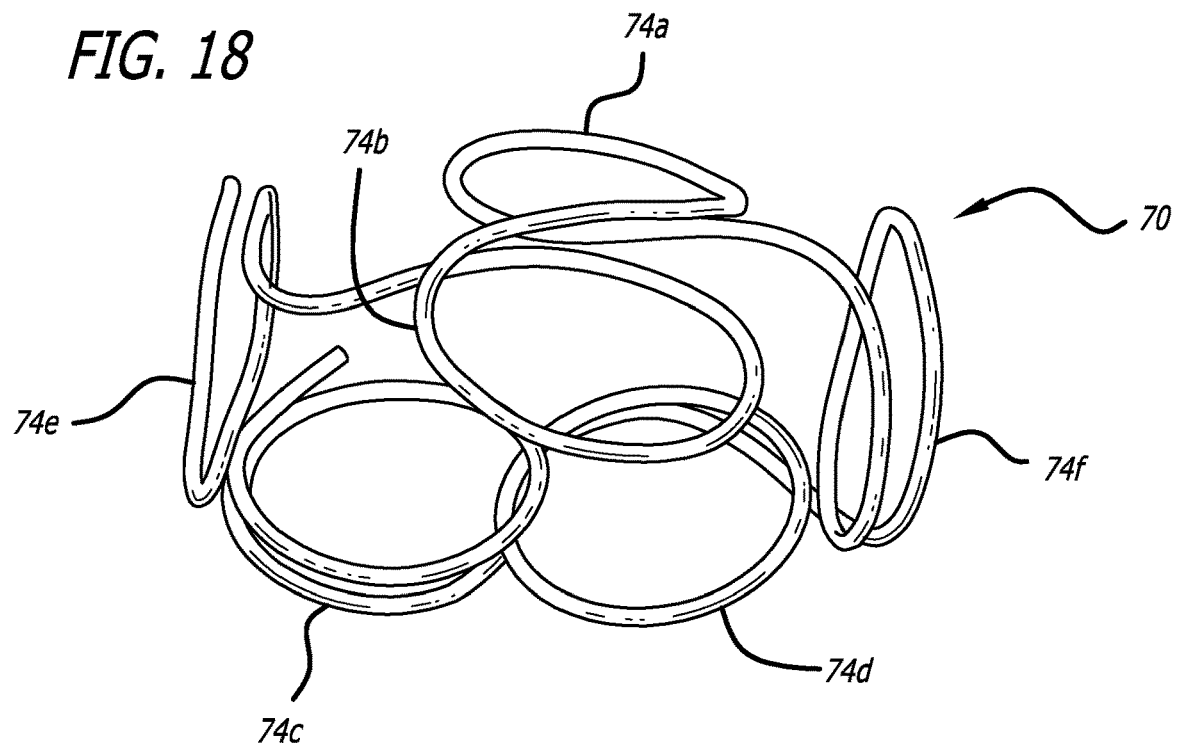
Figure 19:
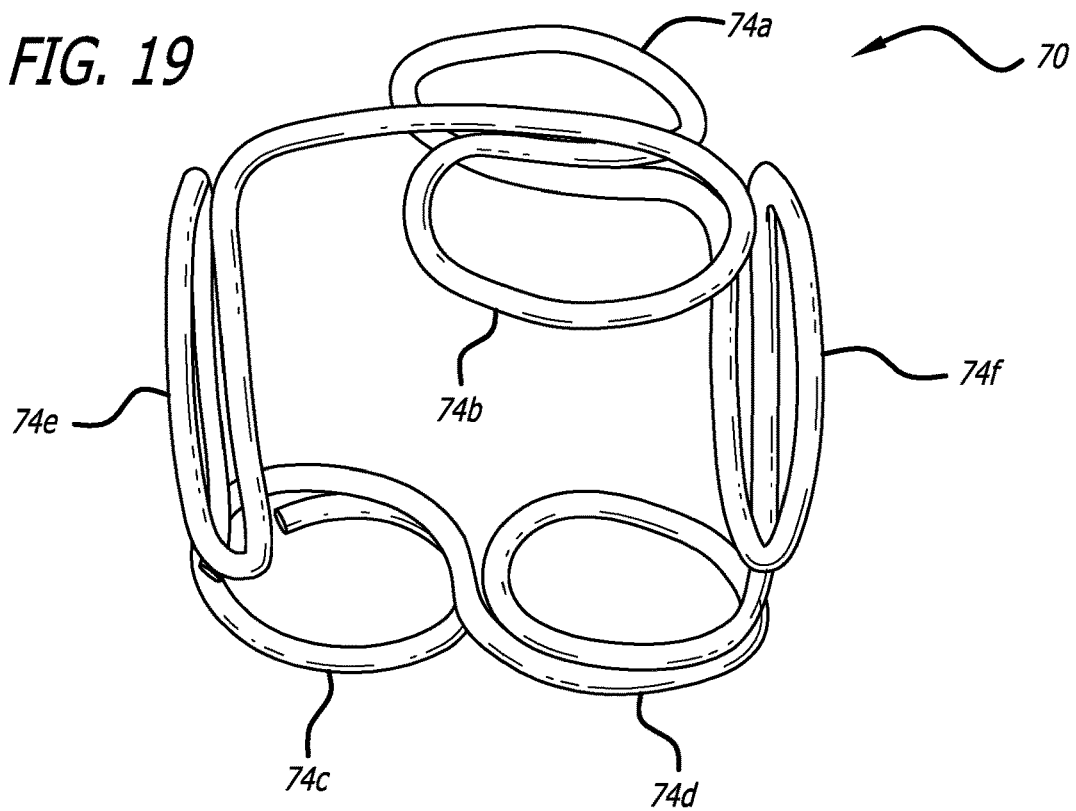

Further complexity may be introduced using the fixture 60 shown in FIGS. 14-15. The fixture 60 in FIGS. 14-15 also has a plurality of pins 62 but differs from the fixture 42 in FIGS. 7 and 8 in three substantive ways. First, the pins 62 extend in directions parallel with x- and y-axes, but there are no pins that extend parallel to a z-axis. Rather, rectangular blocks 64 extend along the z-axis. Second, there are only two concentric pins, 62x₁ and 62x₂ that extend parallel to the x-axis. Third, there are four pins 62y₁₋₄, each having independent longitudinal axes. Winding using the fixture 60 results in complex coils 70 such as those shown in FIGS. 16-19. These figures show a complex coil 70 with first and second loops, 74a and 74b, that are substantially coplanar and arranged in a FIG. 8 pattern, as well as third and forth loops, 74c and 74d that are similarly substantially coplanar and arranged in a FIG. 8 pattern that is rotated from the FIG. 8 pattern of the first and second loops, 74a and 74b. The examples shown in FIGS. 16-19 show the two FIG. 8 patterns rotated 90 degrees relative to each other. Additionally, the complex coils 70 include fifth and sixth loops, 74e and 74f, which are relatively concentric.

After winding, the fixture and complex coil are heat-set by methods known in the art. For example, a typical annealing step for platinum complex coils is approximately 1100° F. for 5-60 minutes.

Once annealed, the complex coil will approximately retain the wound shape when substantially in a minimal energy state. The complex coil may then be subject to further processing such as forming a tip, adding a coupling mechanism for attachment to a delivery system, placing hydrogel or fibers onto or within the complex coil, placing a stretch resistant member inside or outside the complex coil, etc. The complex coil can then be attached to a delivery system, which is well known in the art, such as those disclosed in U.S. patent application Ser. No. 11/212,830, entitled Thermal Detachment System for Implantable Devices, the entirety of which is incorporated by reference hererin. Other examples of delivery systems are disclosed in Guglielmi U.S. Pat. No. 6,010,498 or Gandhi U.S. Pat. No. 6,478,773. Once attached to the delivery pusher, the complex coil 10 is placed in a substantially linear configuration within a tube for delivery to the treatment site.

In the typical procedure, the linear complex coil is fed through a conduit such as a microcatheter by advancing it through the conduit with the delivery pusher. Upon exiting the microcatheter, the complex coil then self-forms into a structure within the treatment site that approximates its annealed shape.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

We claim:

1. A method of forming a complex coil for the treatment of aneurysms, comprising:
    wrapping a coiled wire around a fixture to create a plurality of closed loops that each have a generally "O" shape,
    in which a plane extends entirely across a length and width of each closed loop:
    intersect each other at a common intersection axis near a center of said complex coil such that the plurality of loops form a toroid shape,
    wherein said plurality of closed loops are arranged in a general circular pattern about said common intersection axis to form the toroid shape;
    heat setting said coiled wire in said toroid shape;
    removing said coiled wire from the fixture.

2. The method of claim 1, wherein wrapping said coiled wire around said toroid-shaped fixture comprises passing the coiled wire through a center of the fixture and around an outside of the fixture a plurality of times, thereby forming said plurality of closed loops.

3. The method of claim 2, wherein forming said plurality of closed loops comprises forming four loops around said fixture, each loop spaced approximately 90 degrees from adjacent loops.

4. The method of claim 2, further comprising assessing a size of an aneurysm in which said complex coil is to be placed and determining a number of loops to be formed based said aneurysm size.

5. The method of claim 1, wherein heat setting said coiled wire comprises heating said coiled wire to about 1100 degrees F. for a predetermined period of time.

6. The method of claim 5, wherein heating said coiled wire to 1100 degrees F. for said predetermined period of time comprises heating said coiled wire to 1100 degrees F. for 5 to 60 minutes.

7. The method of claim 1, wherein wrapping said coiled wire around said fixture further comprises forming a first loop around said toroid-shaped fixture, and forming a second loop around said toroid-shaped fixture at about 180 degrees relative to said first loop.

8. The method of claim 7, wherein wrapping said coiled wire around said toroid-shaped fixture further comprises forming a third loop at an angle different than said first loop and said second loop around said toroid-shaped fixture, and forming a fourth loop around said toroid-shaped fixture at about 180 degrees relative to said third loop.

9. The method of claim 8, wherein forming said first loop and said second loop comprises forming a figure 8 shape.

10. The method of claim 9, wherein forming said third loop and said fourth loop comprises forming a figure 8 shape.

11. The method of claim 1, wherein wrapping said coiled wire around said toroid-shaped fixture further comprises forming 2 to 4 loops.

12. The method of claim 1, wherein wrapping said coiled wire around said toroid-shaped fixture further comprises forming 4 to 12 loops.

13. The method of claim 1, wherein wrapping said coiled wire around said toroid-shaped fixture further comprises forming said plurality of closed loops that each have a circle, oval, square, ellipse, or star shape.

14. The method of claim 1, wherein attaching said complex coil to a coupling mechanism for a delivery system.

15. A method of forming a complex coil for the treatment of aneurysms, comprising:
    forming a microcoil around a fixture and into a plurality of closed loops that each form a generally "O" shape, wherein said plurality of closed loops are disposed vertically around a common intersection axis and are each substantially contained within one of a plurality of planes that extend entirely across a length and a width of each of the closed loops; wherein the plurality of planes intersect each other at a common intersection axis near a center of said complex coil, wherein said plurality of closed loops are arranged in a generally circular pattern about said common intersection axis to form the toroid shape; and,
    heat setting a position of said plurality of loops.

16. The method of claim 15, wherein wrapping said forming said microcoil around said fixture further comprises forming a first loop around said fixture, and forming a second loop around said fixture at about 180 degrees relative to said first loop, thereby forming a figure 8 shape.

17. The method of claim 15, wherein wrapping said microcoil around said fixture further comprises forming 4 to 12 loops.

18. A method of forming a complex coil for the treatment of aneurysms, comprising:
    forming plurality of closed loops vertically around a common intersection axis; each of the plurality of closed loops having a circle, oval, square, ellipse, or star shape, and being substantially contained within one of a plurality of planes that extend entirely across a length and a width of each closed loop; wherein each of the planes intersect each other at the common intersection axis; and,
    heat setting a position of said plurality of loops.

* * * * *